United States Patent [19]
Kapp et al.

[11] Patent Number: 5,506,406
[45] Date of Patent: Apr. 9, 1996

[54] METHOD AND APPARATUS FOR DETERMINING THE CONCENTRATION OF A HEAVY ELEMENT IN A ROCK FACE

[75] Inventors: Louis J. Kapp, Hartbeespoort; Gordon I. Procter, Colbyn Pretoria; Edward S. Wesolinski, Pretoria, all of South Africa

[73] Assignee: Atomic Energy Corporation of South Africa Ltd., Pelindaba, South Africa

[21] Appl. No.: 243,370

[22] Filed: May 16, 1994

[30] Foreign Application Priority Data

May 17, 1993 [ZA] South Africa .............................. 93/3415

[51] Int. Cl.$^6$ .................................................. G01N 23/203
[52] U.S. Cl. ............................................. 250/253; 378/88
[58] Field of Search ............................... 378/88; 250/253, 250/255, 252.1 R

[56] References Cited

U.S. PATENT DOCUMENTS

| | | | |
|---|---|---|---|
| 3,829,686 | 8/1974 | Schultz et al. | 250/262 |
| 4,566,114 | 1/1986 | Watt et al. | 378/88 |

FOREIGN PATENT DOCUMENTS

| | | |
|---|---|---|
| 81/69173 | 7/1981 | Australia . |
| 72/9137 | 11/1973 | South Africa . |
| 76/6086 | 7/1977 | South Africa . |
| 79/3784 | 7/1980 | South Africa . |
| 80/0074 | 12/1980 | South Africa . |
| 80/0633 | 2/1981 | South Africa . |
| 79/5087 | 4/1981 | South Africa . |
| 81/2363 | 4/1982 | South Africa . |
| 81/6268 | 1/1983 | South Africa . |
| 86/6868 | 11/1988 | South Africa . |
| 2073884 | 10/1981 | United Kingdom ..................... 378/88 |

OTHER PUBLICATIONS

Wesolinski et al., "A Portable Coal Face Ash Monitor Based on Dual Energy Gamma Radiation", pp. 33–46, Symposium on Nuclear Techniques in the Exploration & Exploitation of Energy and Mineral Resources, Vienna Jun. 5–8, 1990.

*Primary Examiner*—Carolyn E. Fields
*Attorney, Agent, or Firm*—Dressler, Goldsmith, Shore & Milnamow, Ltd.

[57] ABSTRACT

A method of determining the concentration of incombustible material in a predetermined volume of coal includes irradiating the volume with γ-rays from a first source having a first, low energy; and simultaneously irradiating the volume with γ-rays from a second source having a second, higher energy. Rays of back-scattered radiation from the irradiated volume are detected. An analogue signal for each ray that is detected is generated, an amplitude of said signal being representative of the energy of the ray. Each analogue signal is converted into an equivalent digital signal. For all values of signals in a predetermined range, the number of digital signals having the same value that are detected in a predetermined time period is determined and said signals of the same value are stored together to provide a frequency spectrum. The frequency spectrum is processed to provide the concentration of incombustible material in the volume.

13 Claims, 2 Drawing Sheets

METHOD AND APPARATUS FOR DETERMINING THE CONCENTRATION OF A HEAVY ELEMENT IN A ROCK FACE

FIELD OF THE INVENTION

This invention relates to a method and apparatus for determining the relative concentrations of combustible and incombustible material in coal. The coal may be a sample or in a working face in a mine.

SUMMARY OF THE INVENTION

According to a first aspect of the invention, there is provided a method of determining the concentration of incombustible material in a predetermined volume of coal, the method including irradiating the volume with gamma or x-rays from a first source having a first, predetermined energy;

simultaneously irradiating the volume with γ-rays from a second source having a second, predetermined energy, higher than that of the first source;

detecting rays of back-scattered radiation from the irradiated volume;

generating an analogue signal for each ray that is detected, an amplitude of said signal being representative of the energy of the ray;

converting each analogue signal into an equivalent digital signal;

for all values of signals in a predetermined range, determining the number of digital signals having the same value that are detected in a predetermined time period and storing said signals of the same value together to provide a frequency spectrum; and processing the frequency spectrum to provide the concentration of incombustible material in the volume.

By "frequency" is meant the number of events per unit time.

Hence, the method may include counting, in a predetermined time period, the number of analogue signals with amplitudes in predetermined amplitude windows, i.e. two ranges of amplitudes within the frequency spectrum and utilising the count in said two selected windows to determine the concentration of incombustible material in the volume.

The method may include selecting the windows corresponding with the energy regions of the back-scattered radiation from the two sources. Preferably the method includes detecting direct radiation, i.e. non-scattered radiation, and utilising the position of a peak resulting therefrom in the frequency spectrum to determine the position of the two selected windows. Thus, the method may include utilising direct radiation from one of the sources, more particularly, the higher the energy γ-ray source. It will be appreciated that instead, the direct radiation could be provided with a further, dedicated source.

The method may include utilising a source having an energy of less than 100 keV as the first source and utilising a source having an energy of greater than 300 keV as the second source.

Further, the method may include collimating the sources to irradiate a region with a desired face surface area and to shield the detecting means from direct radiation, at least to a predetermined extent. Hence, it will be appreciated that the sources are selectively shielded so that only a predetermined amount of non-absorbed direct radiation from at least one of the sources provides the required peak.

The method may also include calibrating to ascertain the frequency spectrum of radiation detected from a region of the volume in respect of which the concentration of incombustible material is known.

Still further, the method may include effecting standardisation from time to time to compensate for decay in either or both of the sources. This may be done utilising a standardizing member. The same standardizing member may then be utilised from time to time, to determine the effect of any decay in the radiation sources and to compensate therefor when the concentration of incombustible material in a volume of coal is determined.

According to a second aspect of the invention, there is provided an apparatus for determining the concentration of incombustible material in a predetermined volume of coal, the apparatus including a first source of γ or x-rays having a first, predetermined energy for irradiating the volume with said first energy γ or x-rays;

a second source of γ-rays having a second, predetermined energy, higher than that of the energy of the first source, for irradiating the volume with said second energy γ-rays;

a detecting means for detecting rays of back-scattered radiation from the volume;

a signal generating means, responsive to the detecting means, for generating an analogue signal for each ray that is detected, an amplitude of the analogue signal representing the energy of the detected ray;

an analogue to digital conversion means for converting each analogue signal into an equivalent digital signal; and a signal processing means for determining and storing the number of digital signals having the same value that are detected in a predetermined time period for all values of signals in a predetermined range, to provide a frequency spectrum and for processing said frequency spectrum to provide the concentration of incombustible material in the volume.

It will be appreciated that the method and apparatus will provide an indication of the relative amount of combustible material and ash (mainly silicon and aluminium) in the coal in a rock face. Thus, one application of the method and apparatus of the invention is to identify the position of a coal seam in a coal mine by determining the percentage of ash in a working face. It will be appreciated that there are many other applications of the method and apparatus of the invention.

The apparatus is preferably portable.

The first source and the second source may be arranged in a holder. The holder, in turn, may be arranged adjacent the detecting means.

The holder may be of a shielding material substantially to inhibit the escape of radiation from the sources therein but to allow the transmission of a predetermined small percentage of direct radiation from at least one of the sources to impinge on the detecting means.

The holder and the detecting means may each include a collimating means for generating a predetermined radiating cone and a reception cone, respectively.

Further, the holder and the detecting means may be arranged in an angled configuration relative to each other so that the radiation cone of the holder and the reception cone of the detecting means intersect in a desired manner.

The holder and the detecting means may be mounted on a mounting means for locating the holder and the detecting means in spaced relationship relative to a face surface area of the volume being tested.

The first source may be a γ-ray source having an energy of less than 100 keV. The second source may be a γ-ray source having an energy of greater than 300 keV.

Those skilled in the art will appreciate that the extent of scattering of low energy γ-rays be a particular element is strongly related to the atomic number of the element, whereas the extent of scattering of high energy γ-rays is substantially independent of the atomic number of the element being irradiated.

By means of the invention, an apparatus for determining the concentration of coal in a rock face is provided which is sufficiently small and light to be portable; has low power utilisation and is easy to calibrate.

BRIEF DESCRIPTION OF THE DRAWINGS

The invention is now described, by way of an example, with reference to the accompanying drawings, in which.

DETAILED DESCRIPTION OF THE DRAWINGS

Figure 1:
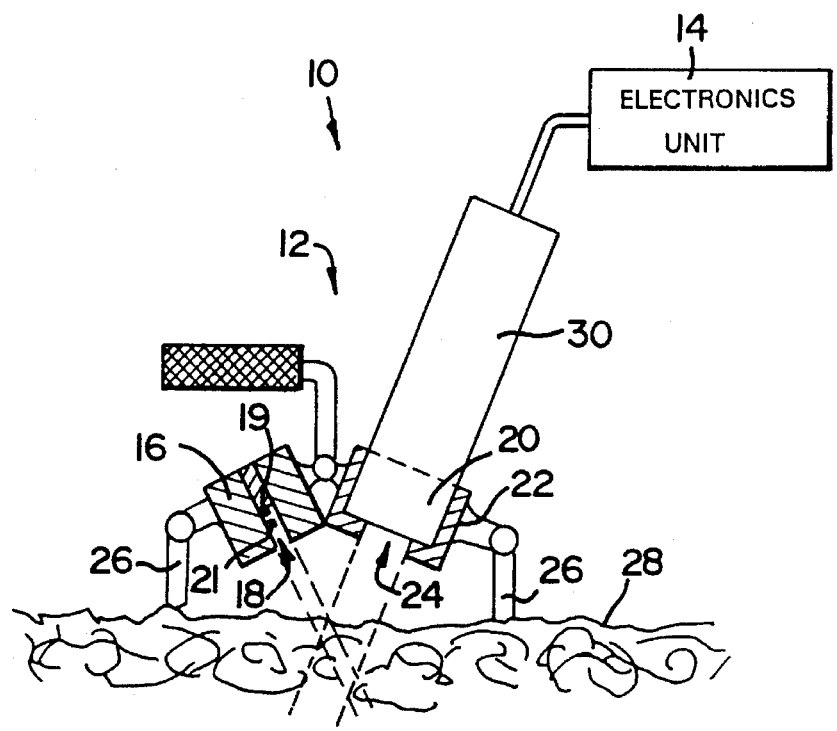
FIG. 1 shows diagrammatically an apparatus in accordance with the invention for determining the concentration of incombustible material in a predetermined value of coal.

Referring to FIG. 1, the apparatus is designated generally by reference numeral 10. The apparatus consists of a hand held probe 12 and an electronics unit 14. The probe 12 has a holder 16 which defines socket 18 to provide a collimated source of both high energy and low energy γ radiation. Thus, two pieces 19, 21 of radio-active material are placed in the base of the socket 18. The holder 16 has a shutter (not shown) which normally closes the mouth of the socket 18 and is manually opened when the apparatus 10 is used.

In the particular embodiment described in FIG. 1, Americium-241 is utilised as the low energy source 21 and Caesium-137 as the high energy source 19. $^{241}$Am provides γ radiation of 60 keV and $^{137}$Cs γ radiation with an energy of 661 keV. Thus, the probe 12 contains a 111 MBq $^{241}$Am source 21 with a 18,5 MBq $^{137}$Cs source 19 mounted directly behind it.

The probe 12 also has a 25 mm×25 mm NaI(Tl) scintillation detector 20. The detector 20 is held in a mount 22 with a collimator 24 to restrict the region "seen" by the detector 20. A photo-multiplier tube 30 is optically coupled to the detector 20. The mount 22 and holder 16 are made of lead or depleted uranium to provide radioactive shielding.

It will be seen that the holder 16 and the mount 22 are angled towards one another. The probe 12 further has three triangularly spaced pins 26 which each have a length of approximately 30 mm. In use, the pins 26 are engaged with the coal face to be sampled so that the γ-ray sources and the detector 20 are substantially a constant distance from the coal face. The pins 26 also protect the detector 20 from damage by the coal face. The holder 16 and the detector 20 are angled so that a radiation cone formed by the collimating socket 18 intersects a reception cone of the detector 20 in a sampled volume which is centrally located relative to the pins 26 and with a scattering angle of about 135°. With the probe 12 the holder 16 is such as to provide an "illuminated" area on the coal face 28, at a distance of 20 mm, having a diameter of approximately 40 mm.

Figure 2:
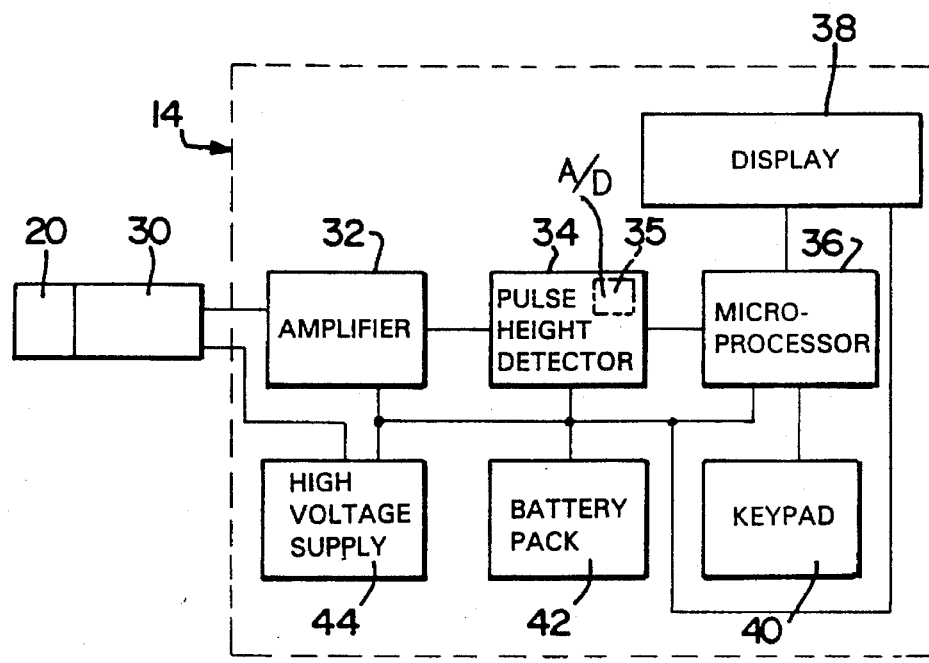
FIG. 2 shows a block diagram of an electronics unit of the apparatus.

Referring to FIG. 2, the electronics unit 14 is now described. The unit 14 has an amplifier 32, a pulse height detector 34, a microprocessor 36, a display readout 38 and a keypad 40. These components are supplied with power from a battery pack 42 which also supplies power to a high voltage supply 44. The detector 20 has a photomultiplier tube 30 which is supplied with power from the high voltage supply 44 and supplies signals to the amplifier 32. The amplifier 32, in turn, supplies output signals to the pulse height detector 34. The pulse height detector 34 incorporates an analogue to digital convertor 35 to provide digital signals to the microprocessor 36. The manner in which the pulse height detector 34 operates and the manner in which the microprocessor 36 processes the signals it receives are described below. The microprocessor 36 then provides a value representative of the concentration of ash (or incombustible material) in the coal face 28, which is displayed on the readout 38.

In use, back-scattered γ-rays directed by the detector 20 cause pulses to be generated by the photomultiplier 30, the amplitude of the pulses being representative of the energy of the γ-rays. These pulses are then amplified by the amplifier 32 and supplied to the pulse height detector 34. The pulse height detector 34 utilises analogue circuitry to determine when the pulse received by it attains a maximum value, to supply a signal proportional to that value for a period of time and to convert such value to a digital signal of a predetermined number or numerical value. Once the microprocessor 36 has received the digital number the pulse height detector is reset and responds to the next pulse it receives. Thus, depending on the maximum value of each pulse, a digital signal of said predetermined numerical value, which lies between 0 and 255, is supplied. The amplifier 32 has a suitable gain so that the maximum pulse height of interest that it receives will provide a digital signal with a numerical value (hereinafter referred to as the "digital value") of "255".

The digital values are supplied to the microprocessor 36. The microprocessor 36 is programmed to provide 256 registers, and to increase the count in the register having the address equal to the digital value received. The registers are cleared at the beginning of a predetermined time period and the various registers incremented upon receipt of the digital values, for the predetermined time period. The address number of each register is directly representative of the height of a particular pulse. For each register, the count in that register agrees with the number of pulses having the amplitude represented by the address of that register. The microprocessor 36 is programmed to perform the accumulation procedure for a predetermined time period, which is the analysis period.

At the end of each analysis period, a frequency spectrum ie. a distribution of the number of pulses as a function of the register addresses is provided in the microprocessor's memory. This distribution is representative of the energy distribution of the γ-rays which caused the pulses. As two different energy sources are used, the frequency spectrum will have two peaks due to back-scattered γ-rays. It will also have a third peak caused by direct radiation from the high energy source due to a small percentage of such radiation transmitted through the shielding.

It will be appreciated by those skilled in the art that the back-scattered γ-rays will be of a lower energy than direct radiation. This energy degradation will be more pronounced for the high energy γ-rays. Thus the three peaks in the frequency spectrum will be in the order of low energy (back-scattered), high energy (back-scattered) and high energy (direct).

Figure 3:
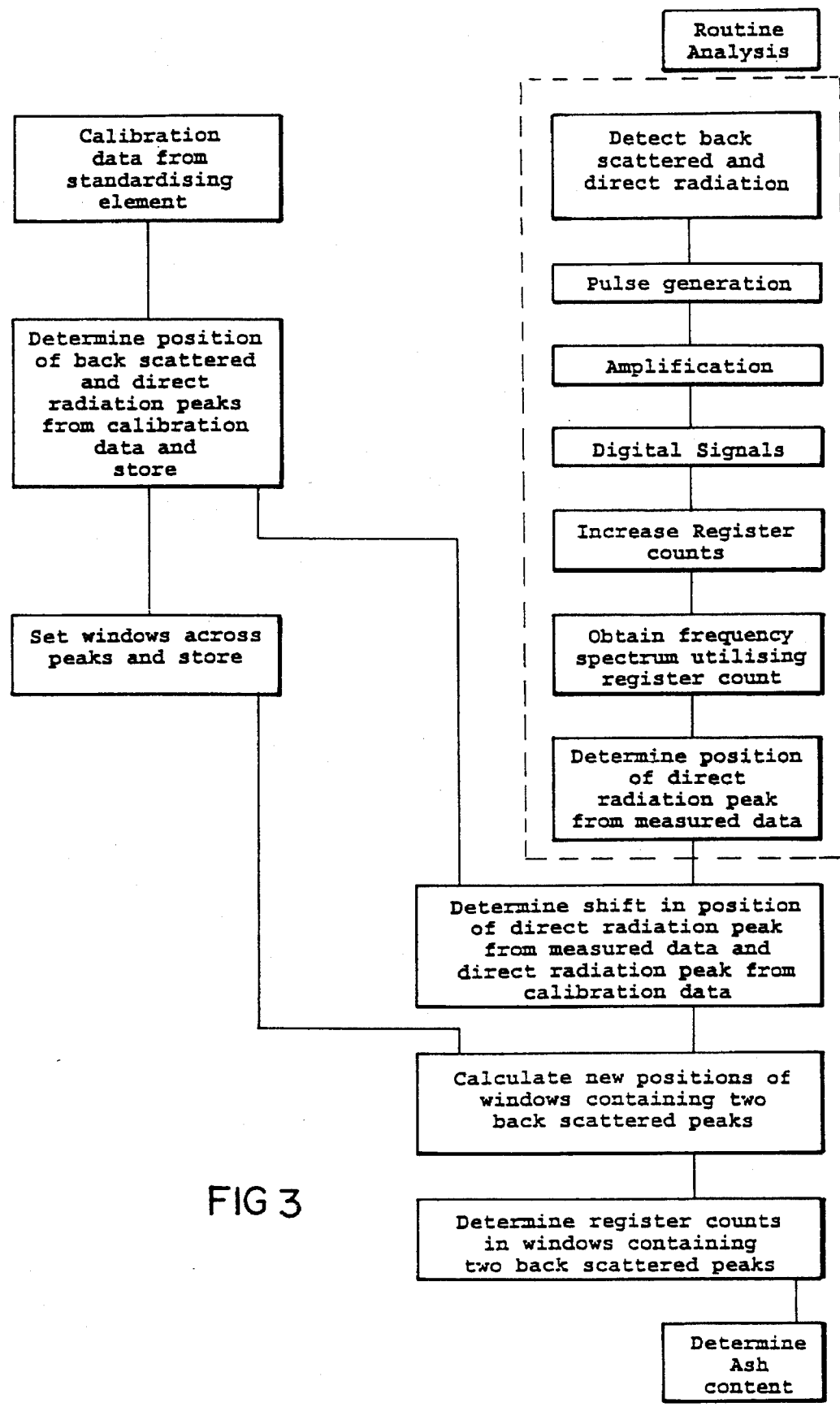
FIG. 3 is a flow chart depicting the process scheme of the present invention.

At the end of each analysis period, the position of each of these peaks is determined utilising suitable software. This is done by determining the position of the third peak (from direct high energy rays) and using that position to calculate the positions of the windows containing the two back-scattered peaks in the frequency spectrum, utilising positional details of the peaks in the frequency spectrum obtained when calibrating. The count number in each of these peaks is also determined by the microprocessor 36. This is done by summing the numbers in the memory positions in the windows. Referring to FIG. 3, the microprocessor 36 then performs a computation using the two totals obtained in accordance with the following formula:

$$\text{Ash content} = m(I_H/I_L) + c$$

where $I_H$=total counts in high energy back-scattered window.

$I_L$=total counts in low energy back-scattered window.

and m and C are predetermined constants.

The result of this computation is representative of the ash content of the sampled volume.

Those skilled in the art will appreciate that with the electronics unit 14 of the invention, variations in amplification factors as a result of, for example, temperature variations are compensated because the peak positions are determined anew in every analysis period.

The apparatus 10 is calibrated by taking a reading in about twenty different places in a coal face. A sample is taken from each place and is analysed in a laboratory to determine the ash content of each sample. The computed values and the analysed values are entered in the microprocessor 36 and stored therein. Using suitable software, the microprocessor 36 performs a straight-line curve fitting technique to obtain the calibrating constants m and C.

When the apparatus 10 is initially calibrated, a standardizing reading is also obtained from a block of acrylic material. This block of acrylic material is subsequently utilised to standardize the apparatus 10 to take into account decay of the radiation sources 19, 21.

It will be appreciated that the electronics unit 14 does not require a plurality of analogue discriminators or the use of any analogue stabilisation techniques to compensate for any gain drifts in the analogue electronic units due to ambient temperature variations.

We claim:

1. A method of determining the concentration of incombustible material in a predetermined volume of coal, the method including:

irradiating the volume with gamma or x-rays from a first source having a first, predetermined energy;

simultaneously irradiating the volume with gamma rays from a second source having a second, predetermined energy, higher than that of the first source;

detecting rays of back-scattered radiation from the irradiated volume;

detecting direct radiation from at least one of the sources;

generating an analogue signal for each ray that is detected, an amplitude of said signal being representative of the energy of the ray;

converting each analogue signal into an equivalent digital signal;

for all values of signals in a predetermined range, determining the number of digital signals having the same value that are detected in a predetermined time period and storing said signals of the same value together to provide a frequency spectrum, the frequency spectrum containing three peaks representing back-scattered radiation from the first source, back-scattered radiation from the second source and direct radiation from said at least one of the sources; and initially irradiating a standardizing element for a predetermined time period, to obtain initial positions of said three peaks and to set windows across the initial positions of each of the two peaks representing back-scattered radiation and, thereafter, utilizing this data to determine any shift in the position of the peaks measured during irradiation of the volume from the initial position of the peaks to calculate new window positions for said two peaks and utilizing counts of signals in the new window positions to determine the concentration of incombustible material in the volume.

2. The method as claimed in claim 1 which includes utilising a source having an energy of less than 100 keV as the first source and utilising a source having an energy of greater than 300 keV as the second source.

3. The method as claimed in claim 1 which includes collimating the sources to irradiate a region with a desired face surface area and to shield the detecting means from direct radiation, at least to a predetermined extent.

4. The method as claimed in claim 1 which includes calibrating to ascertain the frequency spectrum of radiation detected from a region of the volume in respect of which the concentration of incombustible material is known.

5. The method as claimed in claim 1 which includes effecting standardisation from time to time to compensate for decay in either or both of the sources.

6. An apparatus for determining the concentration of incombustible material in a predetermined volume of coal, the apparatus including:

a first source of γ or x-rays having a first, predetermined energy for irradiating the volume with said first energy γ or x-rays;

a second source of γ-rays having a second, predetermined energy, higher than that of the energy of the first source, for irradiating the volume with said second energy γ-rays;

a detecting means for detecting rays of a back-scattered radiation from the volume;

a holder for containing the first source and the second source, the holder being of a shielding material substantially to shield the detecting means from radiation from the sources therein but to allow the transmission of a predetermined percentage of direct radiation from at least one of the sources to be detected by the detecting means;

a signal generating means, responsive to the detecting means, for generating an analogue signal for each ray that is detected, an amplitude of the analogue signal representing the energy of the detected ray;

an analogue to digital conversion means for converting each analogue signal into an equivalent digital signal;

a signal processing means for determining and storing the number of digital signals having the same value that are detected in a predetermined time period for all values of signals in a predetermined range to provide a frequency spectrum, the frequency spectrum containing three peaks representing back-scattered radiation from the first source, back-scattered radiation from the second source and direct radiation from said at least one of the sources; and a memory means for storing data generated from an initial standardizing reading where a standardizing element is irradiated for a predetermined time period, the signal processing means utilizing this data to obtain initial positions of said three peaks and to set windows across the initial positions of each of the two peaks representing back-scattered radiation and to determine any shift in the position of the peaks measured during irradiation of the volume from the initial positions of the peaks to calculate new window positions for said two peaks, and utilizing counts of signals in the windows in said new window positions to determine the concentration of incombustible material in the volume.

7. The apparatus as claimed in claim 6 which is hand held.

8. The apparatus as claimed in claim 6 in which the holder is arranged adjacent the detecting means.

9. The apparatus as claimed in claim 6 in which the holder and the detecting means each include a collimating means for generating a predetermined radiating cone and a reception cone, respectively.

10. The apparatus as claimed in claim 9 in which the holder and the detecting means are arranged in an angled configuration relative to each other so that the radiation cone of the holder and the reception of the detecting means intersect in a desired manner.

11. The apparatus as claimed in claim 6 in which the holder and the detecting means are mounted on a mounting means for locating the holder and the detecting means in spaced relationship relative to a face surface area of the volume being tested.

12. The apparatus as claimed in claim 6 in which the first source is a γ-ray source having an energy of less than 100 keV.

13. The apparatus as claimed in claim 6 in which the second source is a γ-ray source having an energy of greater than 300 keV.

* * * * *